(12) United States Patent
Parris

(10) Patent No.: US 7,740,805 B2
(45) Date of Patent: Jun. 22, 2010

(54) INTEGRATED CMOS-COMPATIBLE BIOCHIP

(75) Inventor: Patrice M. Parris, Phoenix, AZ (US)

(73) Assignee: Freescale Semiconductor, Inc., Austin, TX (US)

( * ) Notice: Subject to any disclaimer, the term of this patent is extended or adjusted under 35 U.S.C. 154(b) by 1028 days.

(21) Appl. No.: 11/095,338

(22) Filed: Mar. 31, 2005

(65) Prior Publication Data

US 2006/0223168 A1   Oct. 5, 2006

(51) Int. Cl.
*B01L 3/00* (2006.01)
(52) U.S. Cl. ..................................... 422/100
(58) Field of Classification Search .................. 422/100
See application file for complete search history.

(56) References Cited

U.S. PATENT DOCUMENTS 6,664,104 B2 * 12/2003 Pourahmadi et al. ..... 435/288.6
7,163,888 B2 *  1/2007 Gehoski et al. ............. 438/627

OTHER PUBLICATIONS

Hoffman et al., "Fully Electronic DNA Detection on a CMOS Chip: Device and Process Issues," IEEE 2002, pp. 19.2.1-19.2.4.
Schasfoort et al., "Field-Effect Flow Control for Microfabricated Fluidic Networks," Science, vol. 286, Oct. 29, 1999, pp. 942-945.
Lee et al., "Surface-Tension-Driven Microactuation Based on Continuous Electrowetting," Journal of Microelectromechanical Systems, vol. 9, No. 2, Jun. 2000, pp. 171-180.
Lee et al., "Addressable Micro Liquid Handling By Electric Control of Surface Tension," IEEE 2001, pp. 499-502.
Yun et al., "A Surface-Tension Driven Micropump for Low-Voltage and Low-Power Operations," Journal of Microelectromechanical Systems, vol. 11, No. 5, Oct. 2002, pp. 454-461.
Thewes, R., et al., "Sensor Arrays for Fully-Electronic DNA Detection on CMOS", 2002 ISSCC Digest of Technical Papers, pp. 350, 351, 473.

* cited by examiner

*Primary Examiner*—Walter D Griffin
*Assistant Examiner*—Bobby Ramdhanie
(74) *Attorney, Agent, or Firm*—Ingrassia, Fisher & Lorenz, P.C.

(57) ABSTRACT

A device for analyzing a fluid sample is provided. The device includes a substrate, a trench formed in said substrate, and a processor. The trench includes a channel, a sample chamber, and a reagent chamber, each in fluid communication with each another. The sample chamber is configured to receive the fluid sample. The processor is integrally formed in the substrate and is in communication with the trench. The processor is configured to analyze the fluid sample. Methods for manufacturing the device are also provided.

20 Claims, 5 Drawing Sheets

INTEGRATED CMOS-COMPATIBLE BIOCHIP

FIELD OF THE INVENTION

The present invention generally relates to a biochip, and more particularly, the integration of microfluidic devices and integrated circuits.

BACKGROUND OF THE INVENTION

Biological samples are utilized in a variety of tests that detect certain characteristics of the sample. For example, biological samples may be used for assessing the donor's health, screening the donor's genetics, or detecting pathogens that may be present in the donor. As technology advances, the demand for quick, accurate, small, and low-cost test devices increases. As a result, test device configurations have appeared in which traditional test equipment, such as glass or plastic slides and plates, have been combined with computers. In these configurations, typically, the biological sample is placed on the slide or in the plate, a reagent is pipetted onto the slide or plate and into the sample to yield a test result, and the test result is then visually detected and manually inputted into the computer for analysis.

In some configurations in which suppliers have attempted to decrease the size of traditional test equipment, microfluidics have been used to move the samples from one section of the equipment to another. In some cases, the microfluidics have been constructed by depositing multiple layers of dielectric material over a substrate to form channels and chambers or by depositing polyimide and negative or positive photoresist. These channels and chambers are typically pressure-driven and configured to move the biological sample and the reagent therethrough so that the sample and reagent contact one another and react to yield a result.

Although the above-mentioned devices may be useful in certain circumstances, they suffer from drawbacks. For example, although the samples and reagents may be pressure-driven through the microfluidic chambers, the analysis and processing of the test results is still manual. Consequently, using the device to obtain a test result may be relatively time-consuming. Moreover, current devices are not capable of performing multiple tests on a sample, wherein the determination of whether to perform the multiple tests depends on a result of a previous test. Additionally, the test device may not be available for use by an average consumer. Specifically, the average consumer may not have access to analysis and processing test equipment that may be necessary to obtain a test result.

Accordingly, it is desirable to have small, accurate, and quick test device that is user-friendly and that may be used by an average consumer. In addition, it is desirable to have a method for making the integrated chip that is relatively simple and inexpensive to implement. Furthermore, other desirable features and characteristics of the present invention will become apparent from the subsequent detailed description of the invention and the appended claims, taken in conjunction with the accompanying drawings and this background of the invention.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Although the invention is described as being used with a biological sample, it will be appreciated that the invention may be configured to be used with any type of fluid sample or solid sample which may be made into an aqueous solution, including non-biological samples. Furthermore, there is no intention to be bound by any theory presented in the preceding background of the invention or the following detailed description of the invention.

Figure 1:
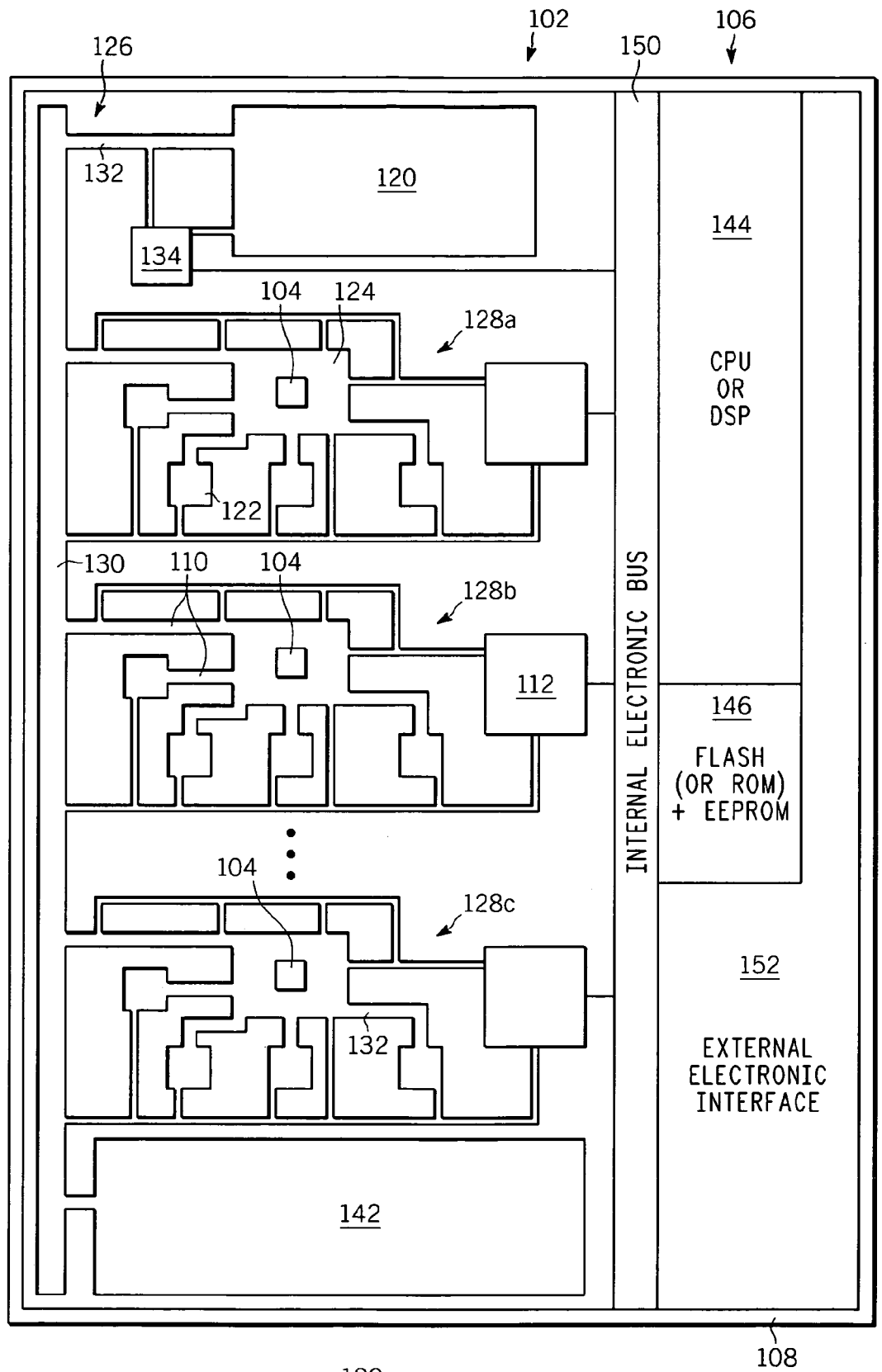
FIG. 1 is a simplified illustration of an exemplary biochip.

FIG. 1 illustrates an exemplary biochip 100. Biochip 100 is configured to receive and analyze a fluid sample. In this regard, biochip 100 includes a microfluidics system 102, sensors 104, and a processor 106. Each of these components is integrated onto a substrate 108, which may be constructed of any conventional material, for example, silicon or silicon-on-insulator, wherein the insulator is any one of a number of insulating materials, such as silicon dioxide, sapphire, and silicon nitride.

Figure 2:
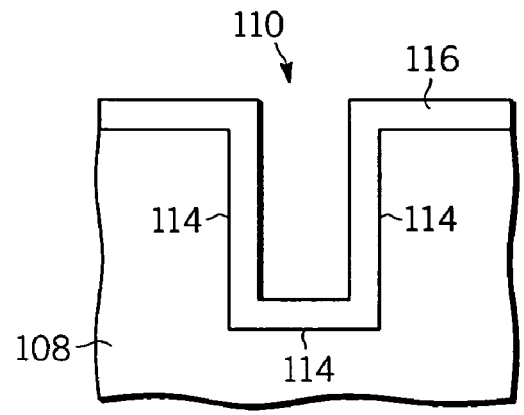
FIG. 2 is a cross-sectional view of an open trench that may be employed in the exemplary biochip of FIG. 1.
Figure 3:
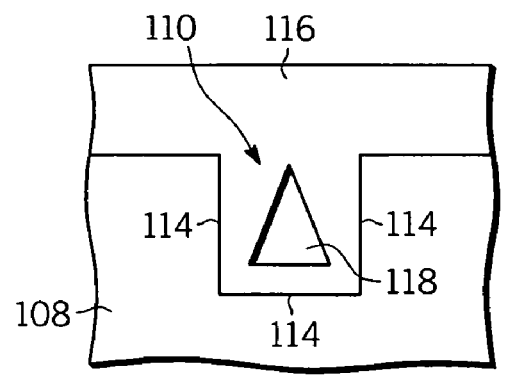
FIG. 3 is a cross-sectional view of an exemplary closed trench that may be employed in the exemplary biochip of FIG. 1.

Microfluidics system 102 is configured to move the fluid sample around biochip 100. Microfluidics system 102 includes a series of trenches 110 and a module controller 112 coupled to at least a portion of trenches 110. Turning to FIG. 2, a cross-sectional view of an exemplary trench 110 is provided. Each trench 110 is formed in substrate 108 and includes walls 114. Preferably, trench 110 has both opened and closed sections. FIG. 2 illustrates an open trench 110 that includes walls 114 having a relatively thin layer of a dielectric material 116 deposited substantially uniformly thereon. In an exemplary embodiment of a closed trench 110, such as shown in FIG. 3, walls 114 include a layer of dielectric material 116 that is non-uniformly deposited thereon and a flowpath 118 is formed through dielectric material 116. Alternatively, a plate having dielectric properties, for example, glass, is disposed over trench 110 to define flowpath 118.

Returning to FIG. 1, trench 110 may have any one of numerous patterns or configurations. No matter the particular configuration, trench 110 preferably includes a sample reservoir 120, at least one reagent reservoir 122, and a mixing reservoir 124. Reservoirs 120, 122, and 124 fluidly communicate with one another via channels 126. Sample reservoir 120 is configured to receive and contain the fluid sample. In one exemplary embodiment, sample reservoir 120 is sized to provide space within which a user may place a drop of the fluid sample, either by using a dropper or, in the case of blood, pricking a finger and allowing the blood to drop into sample reservoir 120. Preferably, sample reservoir 120 is an open section of trench 110. However, it will be appreciated that sample reservoir 120 may, alternatively, be closed and coupled to an open section of trench 110.

Reagent reservoir 122 contains a reagent that is conventionally used in the analysis of the fluid sample. It will be appreciated that a test may require more than one reagent in order to yield a particular test result. In such case, biochip 100 includes an appropriate number of reagent reservoirs 122, and each reagent reservoir 122 is filled with a different reagent. Alternatively, the more than one reagent may be contained in a single reagent reservoir 122, if appropriate. Reagent reservoir 122 is preferably formed in a closed section of trench 110 so that the reagent disposed therein will not be exposed to or contaminated by other fluids or particles. Mixing reservoir 124 is configured to receive the fluid sample and reagent and to provide a chamber within which both can be mixed. Mixing reservoir 124 is preferably formed between sample reservoir 120 and reagent reservoir 122 and may be part of either an open or closed trench 110.

It will be appreciated that microfluidics system 102 may include more than one set of reagent reservoirs and mixing reservoirs, for example, a first set 128a, a second set 128b, and a third set 128c, shown in FIG. 1. In one exemplary embodiment, microfluidics systems 102 includes a single sample reservoir 120 coupled to each of the first set 128a, the second set 128b, and the third set 128c of reagent reservoirs and mixing reservoirs. Sample reservoir 120 fluidly communicates with each of first set 128a, second set 128b, and third set 128c. In this embodiment, each of sets 128a, 128b, and 128c can be configured to run different tests; thus, each reagent reservoir 122 of first set 122a includes reagents needed to conduct a first test, each reagent reservoir 122 of second set 122b includes reagents needed to conduct a second test, and each reagent reservoir 122 of third set 122c includes reagents needed to conduct a third test. The first, second, and third tests are preferably tests that are typically conducted in successive order. For example, if the first test is conducted and yields a first test result, biochip 100 then decides whether to conduct the second test, based upon the first test result. Similarly, if the second test is conducted and yields a second result, biochip 100 determines whether to conduct the third test, based upon the second test result. Although each of sets 128a, 128b, and 128c are depicted in FIG. 1 as having the same configuration, it will be appreciated that some or each may have a different structure or function.

Figure 4:
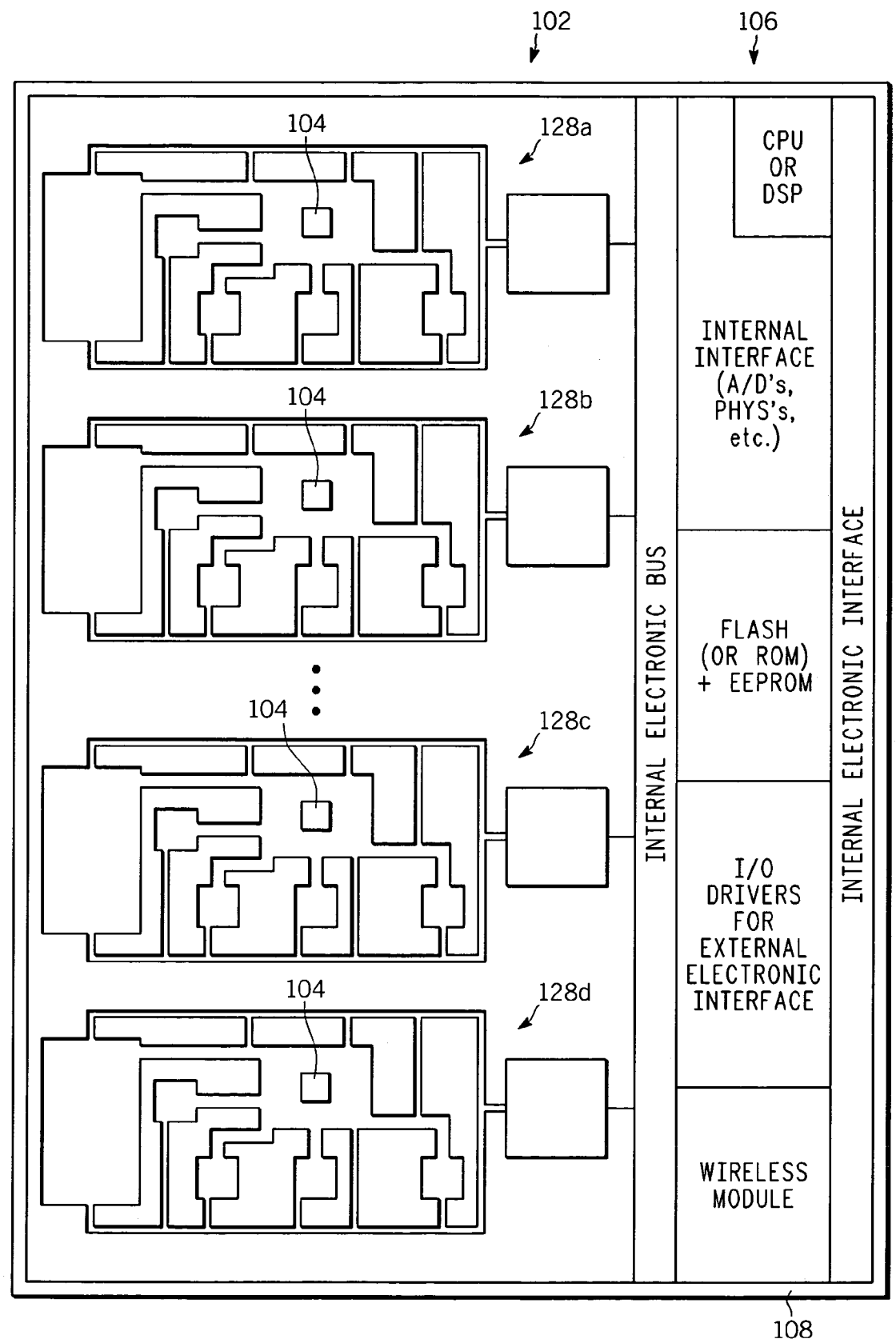
FIG. 4 is a simplified illustration of another exemplary biochip.

Alternatively, as illustrated in FIG. 4, microfluidics system 102 may include multiple sets of sample reservoirs, reagent reservoirs, and mixing reservoirs 128a, 128b, 128c, and 128d. In this embodiment, each of reagent reservoirs 122a, 122b, 128c, and 128d includes different reagents that are together needed to conduct a single test on the fluid sample and each of sets 122a, 122b, 128c, and 128d conducts the same test.

Turning back to FIG. 1, and as briefly mentioned previously, sample reservoir 120, reagent reservoir 122, and mixing reservoir 124 communicate with one another via channels 126. Channels 126 include at least a microfluidic bus channel 130 and capillary channels 132, and fluidly communicate with channel controllers, for example, a sample controller 134 and module controller 112. Microfluidic bus channel 130 couples sample reservoir 120 to mixing reservoir 124 and carries fluid sample therebetween. In other exemplary embodiments, microfluidic bus channel 130 is coupled to capillary channel 132, which allows microfluidic bus channel 130 to provide a path for the fluid sample to mixing reservoir 124. Capillary channels 132 couple reagent reservoir 122 to mixing reservoir 124.

Figure 5:
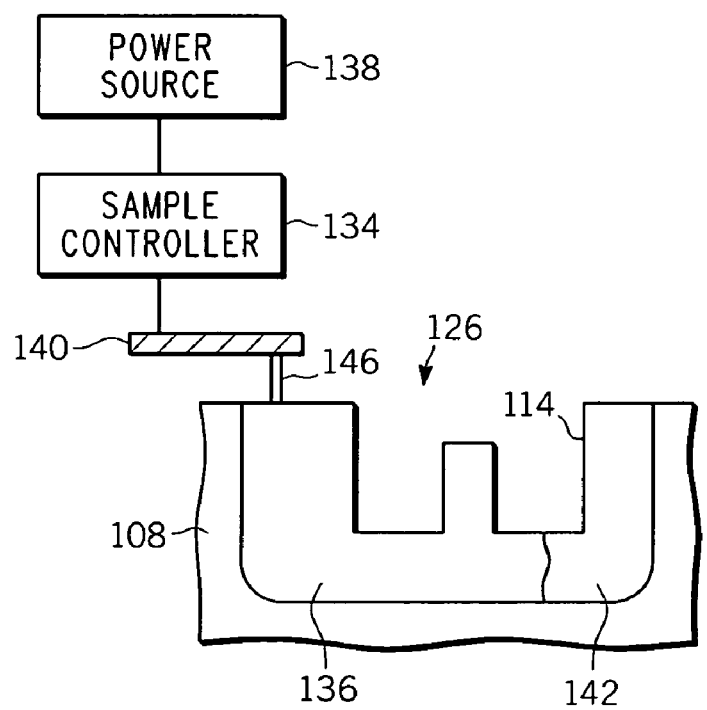
FIG. 5 is a cross-sectional view of a trench having an exemplary controller coupled thereto.
Figure 6:
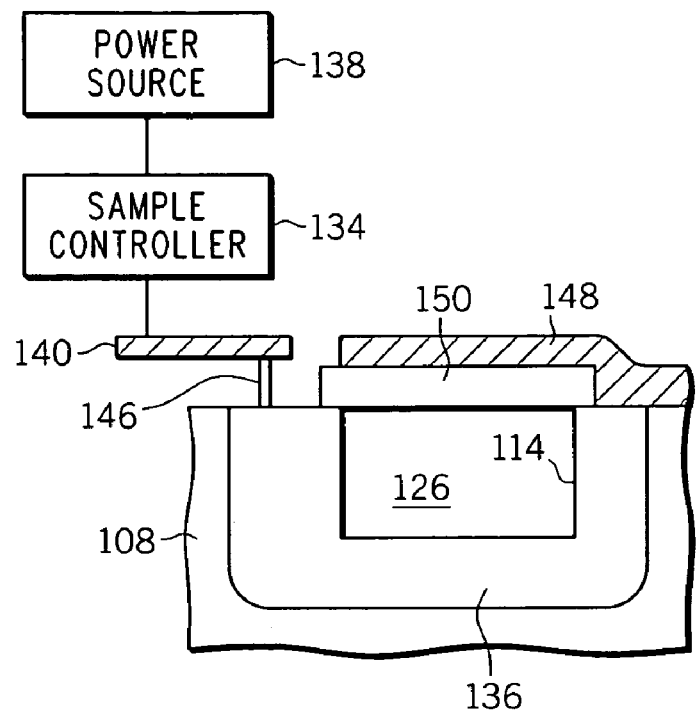
FIG. 6 is a cross-sectional view of a trench having another exemplary controller coupled thereto.

Sample controller 134 controls movement of the fluid sample through channels 126 from sample reservoir 120 to mixing reservoir 124. Sample controller 134 may also be configured to act as a valve and to prevent fluids from freely communicating between sample reservoir 120 and mixing reservoir 124. Sample controller 134 may have any one of numerous suitable configurations. In one exemplary embodiment, illustrated in FIGS. 5-7, sample controller 134 is a circuit that controls at least one doped substrate region 136 and at least one power source 138, which are coupled to one another by a metal line 140 controlled by sample controller 134. Doped substrate region 136 is configured to operate with power source 138 to provide transverse and longitudinal electric fields to thereby cause electrical biasing of fluid that may be proximate thereto. Doped substrate region 136 is implanted into substrate 108 in sufficient proximity to channels 126, for example, in walls 114, or proximate walls 114, to provide electric fields therein. It will be appreciated that doped substrate region 136 may be either n-type material or p-type material, the selection of which may be dependent upon substrate doping and desired bias. Optionally, an extension area 142 of doped substrate region 136 may be included. Extension area 142 provides improved ability to manipulate fluid.

Figure 7:
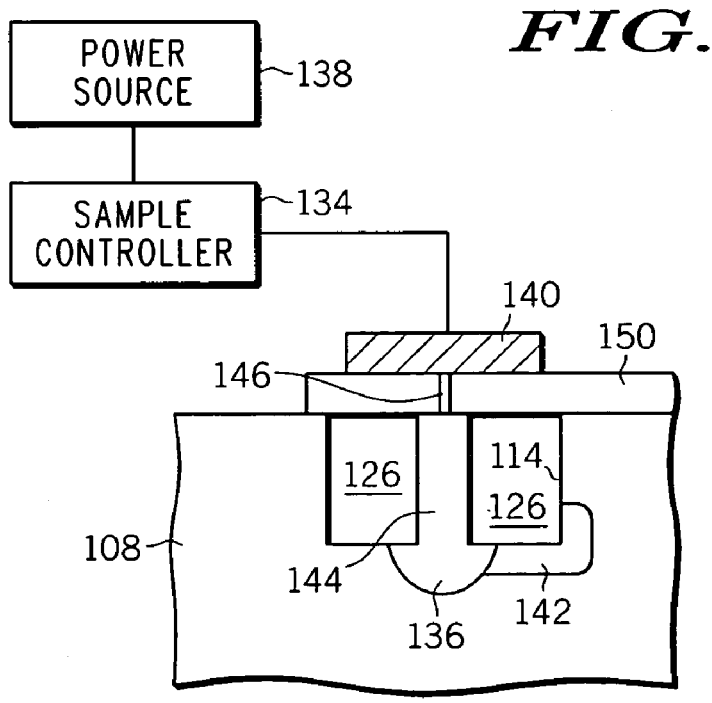
FIG. 7 is a cross-sectional view of a trench having still another exemplary controller coupled thereto.

In another exemplary embodiment, shown in FIG. 7, channel 126 includes a pillar 144 formed in the middle thereof. Pillar 144 provides additional control over the movement of fluid samples by operating with power source 138 to produce electric fields through the middle of channel 126. Pillar 144 is constructed of doped material capable of forming electric fields when current is passed therethrough or an electrical bias is applied. It will be appreciated that any type of suitable doped material, or material capable of doping substrate 108 may be employed, including, but not limited to p-type Si and n-type Si.

Power source 138 may be any one of numerous types of devices capable of supplying power. The supplied power may be either AC or DC power, however, the selection is dependent on the particular configuration and material used in the structure of doped substrate region 136. Thus, when power source 138 supplies power to doped substrate region 136 and/or to pillar 144, an electric field is produced within doped substrate region 136 and within channel 126. Consequently, fluid within channel 126 becomes electrically biased causing or preventing movement through channel 126.

A conductor, exemplified here by metal line 140, is configured to couple power source 138 to doped region 136 and may do so in any one of numerous manners. In one exemplary embodiment, shown in FIG. 5, metal line 140 extends over substrate 108 and contacts doped region 136 by contact 146 to supply electrical biasing to an open channel. In another exemplary embodiment, shown in FIG. 6, metal line 140 contacts doped region 136 via contact 146 and additionally operates with a conductor material 148 overlying a sealing material 150 to thereby cause fluid within channel 126 to move therethrough. In still another exemplary embodiment, such as illustrated in FIG. 7, channel 126 is sealed with sealing material 150 and metal line 140 extends over sealing material 150. Additionally, contact 146 extends through sealing material 150 to couple metal line 140 with pillar 144.

Turning back to FIG. 1, module controller 112 is configured to control movement of fluid from reagent reservoir 122 to mixing reservoir 124 and the amount of reagent that is moved from reagent reservoir 122 to mixing reservoir 124. Module controller 112 preferably has a configuration that is similar to sample controller 134, for example, and controls at least one doped substrate region and power source. However, it will be appreciated that any other device capable of causing movement of reagent through channel 126 may be employed as well. Module controller 112 is coupled to capillary channel 132 and, optionally, coupled to reagent reservoir 122.

Sensor 104 is configured to sense a test result that is obtained after sample and reagent are mixed in mixing reservoir 124 and to transmit the test result to processor 106. In this regard, sensor 104 is coupled to mixing reservoir 124 and is in electrical communication with processor 106. Sensor 104 may be any one of numerous devices configured to sense a measurable chemical, physical, or electrical property that may be useful for fluid sample testing. For example, sensor 104 may include an electrode disposed within mixing reservoir that senses and measures an electrical charge or change in electrical charge emitted by a mixture that is contained therein. The electrical charge may represent a pH measurement, or formation of an ionic fluid. In another example, sensor 104 may include a DNA probe.

As briefly mentioned previously, after sensor 104 senses a test result, it communicates the test result to processor 106. Processor 106 is integrated circuitry configured to analyze the test result and to control biochip 100. Preferably, processor 106 is integrally formed on substrate 108 and electrically communicates with and controls both module controller 112 and sample controller 134. Processor 106 is any standard controller that may be suitable for controlling a microchip and may include standard controlling devices such as a memory 146, other memory modules, computational circuitry, central processing unit ("CPU") 144, an internal electronic bus 150, and an external electronic interface 152.

Memory 146 is configured to store software describing algorithms that instruct biochip 100 to perform certain tests or sets of reactions and pertinent data. In one exemplary embodiment, memory 146 includes instructions that direct microfluidics system 102 to move fluid sample into mixing reservoir 124, move a reagent into mixing reservoir 124 to mix with the fluid sample to obtain a mixture, analyze the mixture to obtain a first test result, and determine whether a second test should be performed on the fluid sample, based upon the first test result. In another exemplary embodiment, memory 146 includes instructions that direct microfluidics system 102 to move a fluid sample into mixing reservoir 124, move a reagent into mixing reservoir 124 to mix with the fluid sample to obtain a mixture, analyze the mixture to obtain a first test result, and indicate the first test result to a user. It will be appreciated that memory 146 may include any other software instructions as well. Memory 146 may be any one of numerous suitable devices, such as, for example, a Flash module+EEPROM, an EEPROM NVM module, and ROM. Memory 146 communicates its stored instructions to CPU 144.

CPU 144 is configured to execute the instructions stored in memory 146. Thus, CPU 144 is coupled between memory 146, sensor 104, module controller 112, and sample controller 134. After CPU 144 receives a START signal from sensor 104 or other internal or external source, CPU 144 causes module controller 112 and sample controller 134 to operate according to the stored instructions in memory 146. The CPU 144 may also be configured to request sensor 104 readings through module controller 112 and non-illustrated internal interfaces, write received data into memory 146, or non-illustrated RAM memory, enforce security of the received data and other data, and cause external electronic interface 152 to communicate received data or test results.

Internal electronic bus 150 serves as an interface between processor 106 and microfluidics system 102. In this regard, internal electronic bus 150 may have any one of numerous conventional configurations capable of providing communication between processor 106 and microfluidics system 102. For example, internal electronic bus 150 may be a conventional multi-bit bus or single multiplexed line.

External electronic interface 152 provides an interface between processor 106 and a non-illustrated external device to which test result data may be communicated. Thus, external electronic interface 152 may be any one of a number of devices conventionally used on a microchip to communicate data. For example, external electronic interface 152 may be a hard-wired electrical input/output interface, or alternatively, a wireless module configured to wirelessly transmit data. The data transmitted by external electronic interface 152 may be received by a non-illustrated computer, or other suitable data-receiving device.

Figure 8:
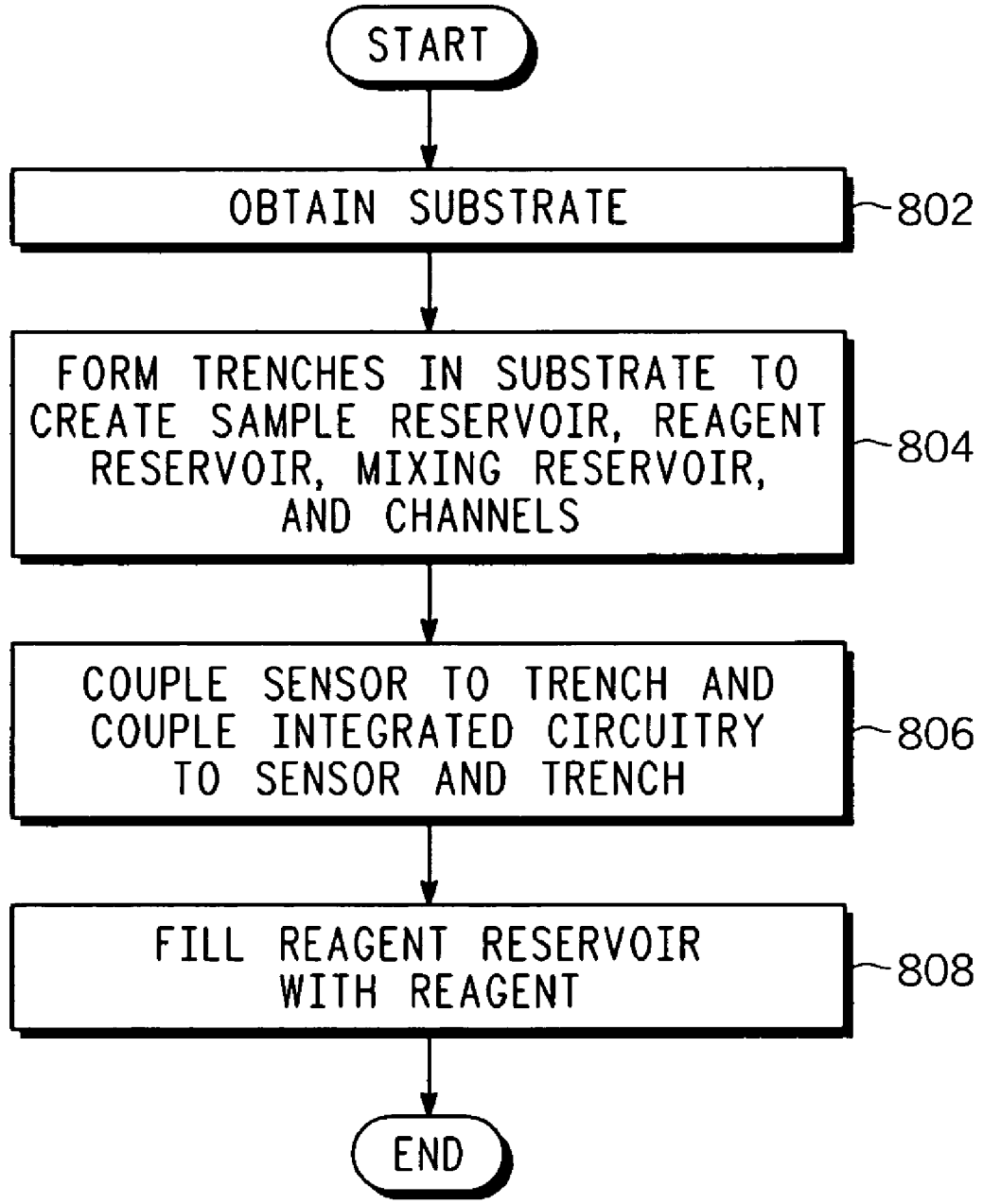
FIG. 8 is a flowchart depicting an exemplary method of manufacturing the exemplary biochip of FIG. 1 and FIG. 4.

Turning now to FIG. 8, an exemplary method for fabricating biochip 100 is provided. The overall process (800) will first be described generally. It should be understood that the parenthetical references in the following description correspond to the reference numerals associated with the flowchart blocks shown in FIG. 8. First, a substrate 108 is obtained (802). Trenches 110 are formed into substrate 108 to form a sample reservoir 120, a reagent reservoir 122, a mixing reservoir 124, and channels 126 (804). Next, at least a portion of trenches 110 is coupled to sensor 104 and sensor 104 is coupled to integrated circuitry (806). Then, reagent reservoir 122 is filled with a reagent (808). Each of these steps will now be described in detail.

As briefly mentioned previously, first, substrate 108 is obtained (802). Substrate 108 may be obtained in any one of numerous fashions, and, if appropriate, may be an off-the-shelf substrate 108 having suitable properties. In one exemplary embodiment, substrate 108 includes integrated circuitry that is pre-printed, pre-deposited, or otherwise integrally formed therein. In another exemplary embodiment, a blank substrate 108 is obtained and the integrated circuitry is subsequently integrated. In still another exemplary embodiment, substrate 108 includes doped regions that are appropriately patterned thereon to make up sample controller 134 and module controller 112.

After substrate 108 is obtained, trenches 110 are formed into substrate 108 (804). Trenches 110 may be formed using any one of a number of manners conventionally used in CMOS fabrication capable of not only forming channels 126, but also forming reservoirs 120, 122, and 124. For example, trenches 110 may be etched into substrate 108 by reactive ion etching ("RIE"). In one exemplary embodiment, trenches 110 are formed by masking chrome onto substrate 108 in a predetermined pattern, then depositing photoresist over substrate 108 and chrome, dry etching to obtain deep trenches 110, and removing the photoresist from substrate 108. In other exemplary embodiments, trenches 110 may be formed by other forms of etching and/or photolithography. In still other exemplary embodiment, trenches ~110 may be formed into substrate 108 while integrated circuitry is being formed thereon.

Trenches 110 may be formed in any section of substrate 108 proximate the integrated circuitry that make up processor 106 such that resultant biochip 100 is relatively small and compact. It will be appreciated that although trenches 110 are described herein as being formed immediately after obtaining substrate 108, other intervening steps may be included as well. In one exemplary embodiment, for example, after substrate 108 is obtained, an interlevel dielectric is disposed over substrate 108 either next to or over the integrated circuitry, and trenches 110 are formed in the interlevel dielectric. In embodiments in which relatively small biochips 100 are preferred, the interlevel dielectric may be disposed over the integrated circuitry, and trenches 110 may be formed in the interlevel dielectric.

In another exemplary embodiment, as discussed briefly above, trench 110 may include a dielectric layer disposed thereon. In such an embodiment, dielectric material, for example, silicon dioxide, plastic, or silicon nitride is deposited over substrate 108. Dielectric material may be directed to deposit into trench 110 or, alternatively, may be deposited over the entirety of substrate 108. Any one of numerous conventional methods may be used, however, preferably, the dielectric material is deposited in thin layers, such as between 500 Å and 5 microns in thickness. For example, the dielectric material may be deposited via chemical vapor deposition, atomic layer deposition, molecular beam epitaxy and spin-on processing. In another exemplary embodiment, the dielectric material is deposited on trench 110 until a portion of trench 110 proximate the surface of substrate 108 is covered with the dielectric material and forms a flowpath in the middle-thereof.

Then, at least a portion of trenches 110 is coupled to sensor 104 and sensor 104 is coupled to integrated circuitry (806). It will be appreciated that sensor 104 may be coupled to trench 110 in any one of numerous conventional manners. For example, sensor 104 may be bonded to, embedded in, or formed in substrate 108. Sensor 104 is electrically coupled to processor 106 in any conventional manner. In one exemplary embodiment, substrate 108 includes conductive material therein and sensor 104 is coupled to one portion of the conductive material while processor 106 is coupled to another portion of the conductive material. In another exemplary embodiment, a conductor is formed in dielectric layers above substrate 108 and coupled to sensor 104 and bus 150.

In any case, reagent reservoir 122 is filled with reagent (808). This step (808) may include selecting a reagent and dispensing the reagent into reagent reservoir 122. The selection of reagent depends on the particular test for which biochip 100 is manufactured. The selected reagent is preferably capable of withstanding temperatures that may be used for manufacturing biochip 100, without denaturing. Reagent may be dispensed into reagent reservoir 122 in any convention manner. For example, a dropper or pipette may be used to drop a predetermined amount of reagent into reagent reservoir 122. In the embodiment in which the trench 110 is covered with the dielectric material and a flowpath is formed therethrough, reagent may be disposed in one section of biochip 100 and then module controller 112 may be used to cause the reagent to migrate therethrough to a desired reagent reservoir 122. It will be appreciated that although the reagent is described herein as being filled immediately after trenches 110 are formed, reagent reservoir 122 may be filled at any other time after trench 110 formation.

Optionally, reagent reservoir 122 is covered to contain reagent therein. Reagent reservoir 122 may be closed in any one of numerous manners. For example, a second interlevel dielectric is deposited over reagent reservoir 122. Alternatively, dielectric material, such as a glass slide or plastic laminate, is coupled to substrate 108 over reagent reservoir 122. In another alternative, a second substrate, for example, a silicon wafer, is coupled to substrate 108 over reagent reservoir 122.

There has now been provided devices and methods for analyzing a fluid sample. In one exemplary embodiment, the device includes a substrate, a trench formed in the substrate, and a process. The trench includes a channel, a sample chamber, and a reagent chamber, each in fluid communication with each another. The sample chamber is configured to receive the fluid sample. The processor is integrally formed in the substrate and is in communication with the trench. The processor is configured to analyze the fluid sample. The device may further comprise a dielectric layer deposited over at least a portion of the trench to thereby define said reagent chamber. The processor of the device may further comprise a memory module, computational circuitry, and a wireless module, electrically coupled to each other. The substrate of the device may further include a sensor disposed in the trench and in electrical communication with the processor, where the sensor is configured to sense electrical differentials within said trench. The device may also include an internal electronic bus coupled between said processor and said sensor. The device may also include a channel controller in communication with the channel and in communication with the processor, where the channel controller is configured to provide an electrical bias between a first section of the channel and a second section of the channel to thereby move fluid therebetween. The channel controller of the device may be further configured to provide an electrical bias between the first section of said channel and the second section of the channel to thereby prevent movement of fluid therebetween. Alternatively, the channel controller may comprise doped material, a power source, and a metal line, wherein the doped material is integrally formed in the substrate proximate the trench and is coupled to the metal line. The trench of the device may include a mixing chamber coupled between the sample chamber and reagent chamber. The device may further include a reagent disposed within the reagent chamber.

In another exemplary embodiment, a device for analyzing a fluid sample is provided that comprises a substrate, a trench, a sensor, a processor, a channel controller, and a reagent. The trench is formed in the substrate. The trench includes a channel, a sample chamber, and a reagent chamber, each in fluid communication with one another. The sample chamber is configured to receive the fluid sample. The sensor is disposed in the trench and is configured to sense electrical differentials therein. The processor is integrally formed in the substrate and in communication with the sensor. The processor is configured to analyze the fluid sample. The channel controller is in communication with the channel and in communication with the processor. The channel controller is configured to provide an electrical bias between a first section of the channel and a second section of the channel to thereby move fluid therebetween. The reagent is disposed within said reagent chamber.

In still another exemplary embodiment, a method is provided for manufacturing a device used for analysis of a fluid sample using a substrate having a processor integrally formed therein, the processor configured to analyze the fluid sample. The method includes forming a trench in the substrate to form a sample reservoir, reagent reservoir, mixing reservoir, and channels, placing at least a portion of a sensor within said trench, said sensor configured to sense electrical differentials within said trench, and coupling said processor to said trench and said sensor. The method may also include depositing dielectric material into said trench. Alternatively, the step of depositing may comprise depositing dielectric material into the trench to substantially uniformly coat the trench. In another embodiment, the step of depositing comprises depositing dielectric material into a bottom of the trench and onto the substrate around the trench until a passage is formed through the dielectric material. In another embodiment, the method further includes integrating doped silicon into the substrate proximate said trench. The method may also include the step of depositing a conducting material, like metal, in contact with said doped silicon. The method may also include coupling said deposited metal to a power source. The step of etching may include masking chrome onto said substrate in a predetermined pattern, depositing photoresist over said substrate and chrome, performing dry etching to obtain said trenches, and removing said photoresist from said substrate. The method may also include filling the reagent reservoir with a reagent.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method of manufacturing a device used for analysis of a fluid sample, the method comprising:
    forming a trench in a substrate to form a sample reservoir configured to receive the fluid sample, a reagent reservoir configured to contain a reagent, a mixing reservoir including a chamber configured to receive and mix the fluid sample and the reagent to form a mixture, and channels between the sample reservoir, the reagent reservoir, and the mixing reservoir;
    placing at least a portion of a sensor within the chamber, the sensor configured to sense, within the chamber, a measurable property of the mixture to generate a test result, wherein the measurable property is a property selected from a group of properties that includes a chemical property of the mixture, a physical property of the mixture, and an electrical property of the mixture; and
    coupling a processor to the sensor, wherein the processor is integrally formed with the substrate and is configured to analyze the test result.

2. The method of claim 1, further comprising depositing dielectric material into said trench.

3. The method of claim 2, wherein the step of depositing further comprises depositing dielectric material into said trench to uniformly coat said trench.

4. The method of claim 2, wherein the step of depositing comprises depositing dielectric material into a bottom of said trench and onto the substrate around said trench until a passage is formed through said dielectric material.

5. The method of claim 1, further comprising integrating doped silicon into the substrate proximate said trench.

6. The method of claim 5, further comprising contacting a conducting material to said doped silicon.

7. The method of claim 6, further comprising coupling said conducting material to a power source.

8. The method of claim 1, wherein the step of forming the trench comprises:
    masking chrome onto the substrate in a predetermined pattern;
    depositing photo resist over the substrate and chrome;
    performing dry etching to obtain said trench; and
    removing said photo resist from the substrate.

9. The method of claim 1, further comprising filling the reagent reservoir with the reagent.

10. A method of manufacturing a device used for analysis of a fluid sample, the method comprising:
    integrally forming a processor in a substrate, wherein the processor is configured to analyze a test result from a test performed on the fluid sample;
    forming a trench in the substrate to form a reagent reservoir configured to contain a reagent, a mixing reservoir including a chamber configured to receive and mix the fluid sample and the reagent to form a mixture, a channel, and a sample reservoir configured to receive the fluid sample, wherein the channel is formed to provide fluid communication between the reagent reservoir, the mixing reservoir, and the sample reservoir;
    placing at least a portion of a sensor within the chamber, the sensor configured to sense an electrical charge of the mixture that includes the fluid sample within the chamber to generate the test result based on sensing the electrical charge, and to transmit the test result to the processor; and
    coupling the processor to the sensor.

11. The method of claim 10, further comprising integrating doped silicon into the substrate proximate said trench.

12. The method of claim 11, further comprising contacting a conducting material to said doped silicon.

13. The method of claim 12, further comprising coupling said conducting material to a power source.

14. The method of claim 10, wherein the step of forming the trench comprises:
    masking chrome onto the substrate in a predetermined pattern;
    depositing photoresist over the substrate and chrome;
    performing dry etching to obtain said trench; and
    removing said photo resist from the substrate.

15. A method of manufacturing a device used for analysis of a fluid sample, the method comprising:
    forming a trench in a substrate to form a sample reservoir configured to receive the fluid sample, a reagent reservoir configured to contain a reagent, a mixing reservoir including a chamber configured to receive and mix the fluid sample and the reagent to form a mixture, and channels configured to provide fluid communication between the sample reservoir, the mixing reservoir, and the reagent reservoir;
    integrating doped silicon into the substrate proximate the trench;
    placing at least a portion of a sensor within the chamber, the sensor configured to sense, within the chamber, a measurable property of a mixture that includes the fluid sample in order to generate the test result, wherein the measurable property is a property selected from a group of properties that includes a chemical property of the mixture, a physical property of the mixture, and an electrical property of the mixture;
    coupling a processor to the sensor, wherein the processor is integrally formed in the substrate; and
    coupling a channel controller to the doped silicon and to a power source, wherein the channel controller is configured to provide an electrical bias between a first channel of the channels and a second channel of the channels to move the fluid sample from the sample reservoir to the mixing reservoir.

16. The method of claim 15, further comprising depositing dielectric material into said trench.

17. The method of claim 1, wherein the sensor is configured to sense an electrical charge of the mixture that represents a pH measurement.

18. The method of claim 1, wherein the sensor is configured to sense an electrical charge of the mixture that represents formation of an ionic fluid.

19. The method of claim 1, wherein the sensor is configured to sense a change in an electrical charge of the mixture.

20. The method of claim 1, wherein the sensor is a DNA probe.

* * * * *